(12) United States Patent
Yun et al.

(10) Patent No.: US 7,449,580 B2
(45) Date of Patent: Nov. 11, 2008

(54) METHOD OF PREPARING THIENO[3,2-C]PYRIDINE DERIVATIVES AND INTERMEDIATES USED THEREIN

(75) Inventors: Sangmin Yun, Seongnam-si (KR); Eun Sook Kim, Seoul (KR); Hee Seock Kim, Daejeon (KR); Tae Hee Ha, Suwon-si (KR); Kwee-Hyun Suh, Suwon-si (KR); Gwan Sun Lee, Seoul (KR)

(73) Assignee: Hanmi Pharm. Co., Ltd, Kyungki-do (KR)

( * ) Notice: Subject to any disclaimer, the term of this patent is extended or adjusted under 35 U.S.C. 154(b) by 79 days.

(21) Appl. No.: 10/598,790

(22) PCT Filed: Mar. 3, 2005

(86) PCT No.: PCT/KR2005/000586

§ 371 (c)(1),
(2), (4) Date: Sep. 12, 2006

(87) PCT Pub. No.: WO2005/087779

PCT Pub. Date: Sep. 22, 2005

(65) Prior Publication Data

US 2007/0197789 A1    Aug. 23, 2007

(30) Foreign Application Priority Data

Mar. 12, 2004   (KR) .................. 10-2004-0016714

(51) Int. Cl.
*C07D 495/04*    (2006.01)
(52) U.S. Cl. .................. 546/114; 549/50; 549/78
(58) Field of Classification Search ............... 546/114; 549/78, 79, 29, 50
See application file for complete search history.

(56) References Cited

U.S. PATENT DOCUMENTS 5,204,469 A    4/1993   Descamps et al.

FOREIGN PATENT DOCUMENTS

| EP | 555153 A1 | 2/1993 |
| WO | WO 9851689 A1 | 11/1998 |
| WO | WO 0043397 A1 | 7/2000 |
| WO | WO 02059128 A2 | 8/2002 |
| WO | WO 02094802 A1 | 11/2002 |

*Primary Examiner*—Bernard Dentz
*Assistant Examiner*—David E Gallis
(74) *Attorney, Agent, or Firm*—Sughrue Mion, PLLC

(57) ABSTRACT

Ticlopidine and clopidogrel having high blood platelet aggregation inhibitory and anti-thrombotic activities are simply prepared by reacting a substituted thiophene derivative with a 2-chlorobenzylamine derivative.

11 Claims, No Drawings

METHOD OF PREPARING THIENO[3,2-C]PYRIDINE DERIVATIVES AND INTERMEDIATES USED THEREIN

FIELD OF THE INVENTION

The present invention relates to a method of preparing thieno[3,2-c]pyridine derivatives and intermediates used therein.

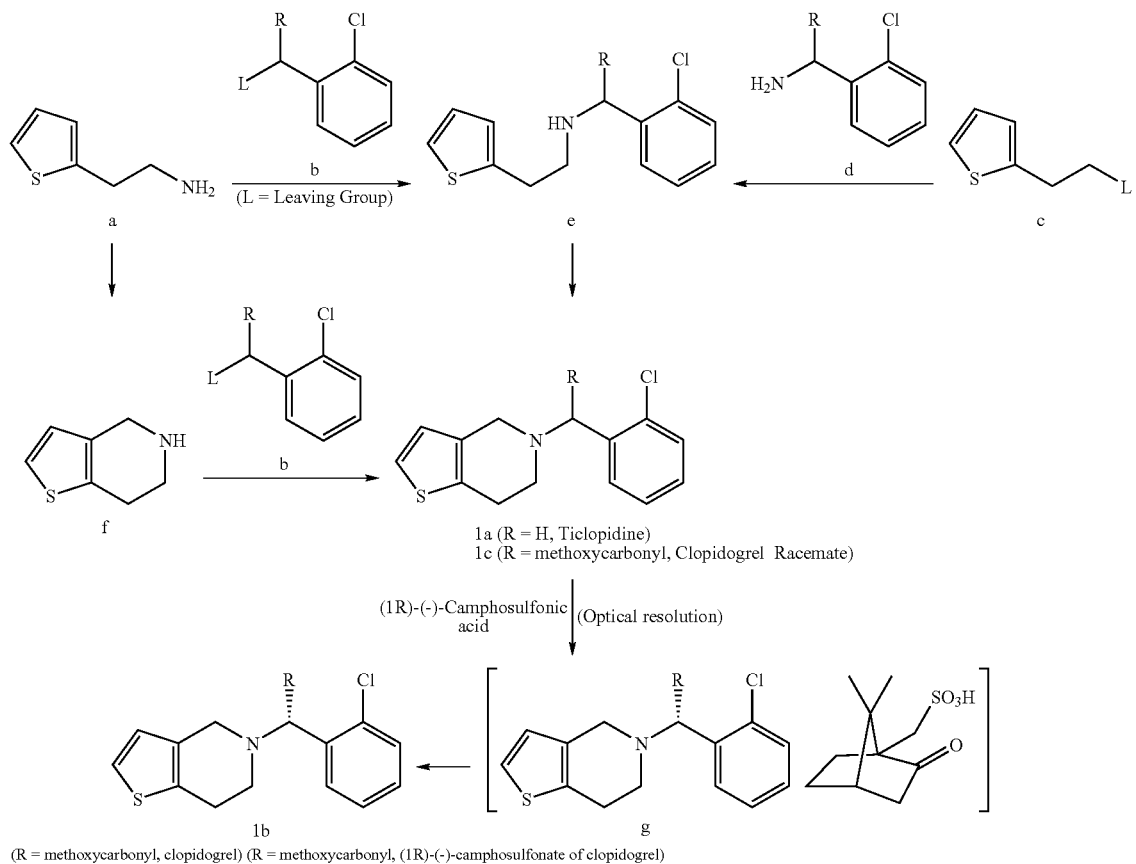

BACKGROUND OF THE INVENTION

Thieno[3,2-c]pyridine derivatives of formula (1) are known to exhibit high blood platelet aggregation inhibitory and anti-thrombotic activities and can be beneficially used as a blood circulatory drug in the treatment of peripheral artery diseases such as cerebral apoplexy, thrombus, and embolism, or coronary artery diseases such as myocardial infarction and angina pectoris:

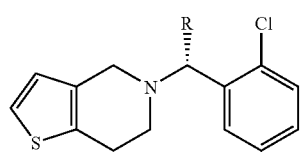

(1)

wherein R is hydrogen or methoxycarbonyl.

The compound of formula (1) wherein R is hydrogen is called ticlopidine, and the compound of formula (1) wherein R is methoxycarbonyl is called clopidogrel (see U.S. Pat. Nos. 4,051,141, 4,529,596 and 4,847,265).

Ticlopidine and clopidogrel have been hitherto synthesized by methods collectively shown in Reaction Scheme A (see U.S. Pat. Nos. 4,127,580, 4,174,448, 6,043,368, 4,529,596, 4,847,265 and 5,204,469, British Patent No. 2,166,730, European Patent Publication No. 0 522 956 A, and International Publication Nos. WO 98/51689 and WO 02/59128):

As shown in Reaction Scheme 1, ticlopidine of formula (1a) may be synthesized by reacting 2-(2-aminoethyl)thiophene of formula (a) with a compound of formula (b) (wherein L represents a leaving group such as chloro) or reacting a compound of formula (c) (wherein L represents a leaving group such as p-toluenesulfonyl) with a o-chlorobenzylamine derivative of formula (d), to obtain a compound of formula (e), and then cyclizing the compound (e) with a formylating agent such as formaldehyde, A-CH$_2$-B (wherein A represents a halogen, alkoxy, alkylthio or amino group, and B represents an alkoxy, alkylthio, amino or alkoxycarbonyloxy group) or a heterocyclic compound of formula

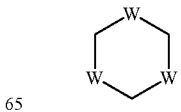

wherein W represents O, NH or S.

Alternatively, ticlopidine of formula (1a) may also be synthesized by directly cyclizing 2-(2-aminoethyl)thiophene of formula (a) with a formylating agent to obtain 4,5,6,7-tetrahydrothieno[3,2-c]pyridine of formula (f), and then reacting the compound (f) with a compound of formula (b).

Analogously, clopidogrel racemate of formula (1c) can be obtained according to the above method, but the racemate must be converted into the optically pure clopidogrel of formula (1b) through a complicated optical resolution process which comprises reacting the racemate of formula (1c) with an optically-active acid, e.g., (1R)-(−)-camphosulfonic acid, to obtain a diastereoisomeric salt of formula (g), subjecting the diastereomeric salt to a series of fractional crystallization processes to increase the optical purity, and then removing the residual optically-active acid from the product. Thus, this method produces the compound of formula (1b) at a low yield.

Accordingly, the present inventors have been studied to develop a simple method of preparing an optically pure clopidogrel, and found that when a specified thiophene derivative is reacted with an optically active 2-chlorobenzylamine derivative, the optically pure clopidogrel can be obtained at a high yield in a simple manner together with ticlopidine.

SUMMARY OF THE INVENTION

It is, therefore, a primary object of the present invention to provide a novel method of preparing an optically pure clopidogrel in a simple manner.

It is another object of the present invention to provide novel intermediates used in the inventive method.

In accordance with one aspect of the present invention, there is provided a method for preparing a thieno[3,2-c]pyridine derivative of formula (1), comprising reacting a compound of formula (2e) with a compound of formula (3):

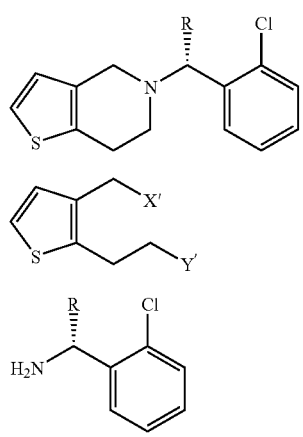

wherein,

R is hydrogen or methoxycarbonyl; and

X' and Y' are each independently chloro, bromo, methanesulfonyloxy or p-toluenesulfonyloxy.

In accordance with another aspect of the present invention, there is provided a compound of formula (2) used in the preparation of the compound of formula (1) as an intermediate:

wherein, $R_1$ is hydrogen, $CH_2X$ or $CO_2R_3$ and $R_2$ is $CH_2Y$, $CO_2R_4$ or $CH_2OR_5$, or $R_1$ and $R_2$ are fused with each other to form —$CH_2$—O—$CH_2$—, where X and Y are each independently hydroxy, chloro, bromo, methanesulfonyl or p-toluenesulfonyl; $R_3$ and $R_4$ are each independently hydrogen, or straight or branched $C_{1-6}$ alkyl; $R_5$ is $C_{1-4}$ alkoxymethyl such as methoxymethyl, ethoxymethyl or 2-methoxyethoxymethyl, with proviso that when $R_1$ is hydrogen, $R_2$ is not hydroxymethyl.

In the present invention, the compound of formula (2e) may be obtained by (i) cyclizing a compound of formula (4) to obtain a compound of formula (2a), reducing the compound of formula (2a) with a reducing agent to obtain a compound of formula (2b) and reacting the compound of formula (2b) with a halogenating or sulfonylating agent, or (ii) cyclizing directly 2-thiopheneethanol with a formylaing agent to obtain a compound of formula (2d), or reacting 2-thiopheneethanol with dialkoxymethane to obtain a compound of formula (2c) and cyclizing the compound of formula (2c) to obtain the compound of formula (2d), and then reacting the compound of formula (2d) with a halogenating agent:

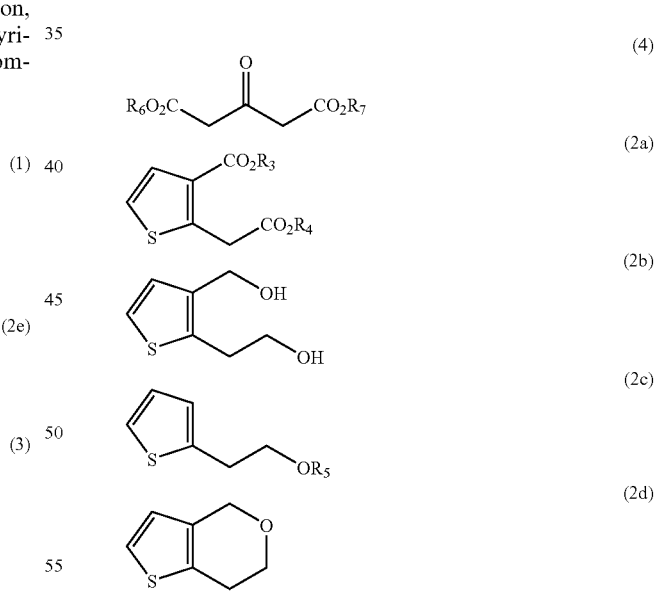

wherein, $R_3$ and $R_4$ are each independently hydrogen, or straight or branched $C_{1-6}$ alkyl, $R_5$ is $C_{1-4}$ alkoxymethyl such as methoxymethyl, ethoxymethyl or 2-methoxyethoxymethyl, and $R_6$ and $R_7$ are each independently straight or branched $C_{1-6}$ alkyl.

DETAILED DESCRIPTION OF THE INVENTION

The present invention as a whole may be represented by Reaction Schemes 2 to 4. Reaction Schemes 2 and 3 show an embodiment of the procedures of preparing the compound of formula (2) used as an intermediate in the inventive method, while Reaction Scheme 4 shows the procedure of preparing the compound of formula (1).

presence of a base to obtain the thiophene-dicarboxylic acid of formula (2a-2), the compound of formula (2) wherein $R_1$ and $R_2$ are $CO_2R_3$ and $CO_2R_4$, respectively, and $R_3$ and $R_4$ are hydrogen.

The solvent used in this step may be a mixture of water and an organic solvent such as a $C_{1-4}$ alcohol and acetone.

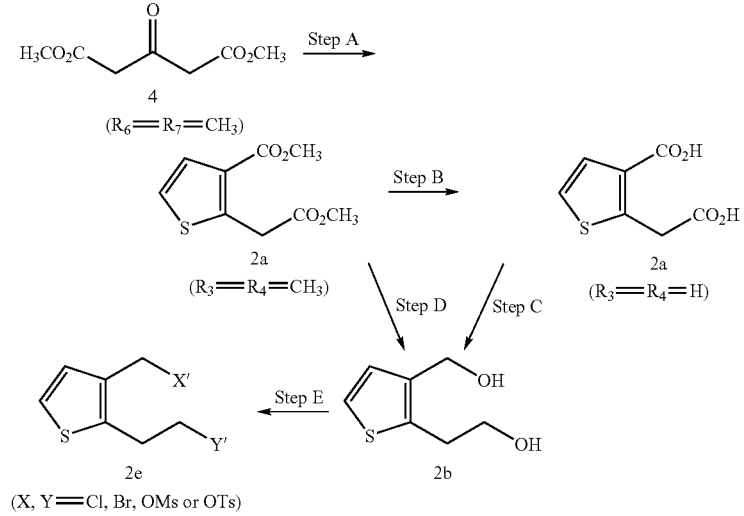

Reaction Scheme 2

(X, Y = Cl, Br, OMs or OTs)

<Step A>

First, in step A, acetone dicarboxylate of formula (4) is allowed to react with 2,5-dihydroxy-1,4-dithiane, which is a dimmer of mercaptoacetaldehyde, in the presence of a Lewis acid catalyst and a solvent to obtain the thiophene-diester compound of formula (2a-1), the compound of formula (2) wherein $R_1$ and $R_2$ are $CO_2R_3$ and $CO_2R_4$, respectively, and $R_3$ and $R_4$ are methyl.

The solvent used in this step may be a protic or aprotic solvent or a mixture thereof, and specific examples thereof includes water, a $C_{1-4}$ lower alcohol, tetrahydrofuran, 1,4-dioxane, 1,2-dimethoxyethane, acetonitrile, propionitrile, butyronitrile, methyl butyrate, isopropyl acetate, butyl acetate and toluene. Dioxane, acetonitrile and propionitrile are particularly preferred.

Representative examples of the Lewis acid catalyst may be indium(III) chloride, indium(III) bromide, indium(III) triflate, magnesium bromide, lithium bromide, lithium chloride and tin(IV) chloride, and particularly, lithium bromide and lithium chloride are preferred. The catalyst may be employed in an amount of 0.01 to 1 molar equivalent, preferably 0.1 to 0.2 molar equivalent, based on the amount of the acetone dicarboxylate of formula (4).

2,5-dihydroxy-1,4-dithiane may be employed in an amount of 0.5 to 1 molar equivalent based on the amount of the acetone dicarboxylate of formula (4).

The reaction may be carried out at a temperature ranging from room temperature to the boiling point of the solvent used, preferably from 50° C. to the boiling point of the solvent.

<Step B>

Subsequently, in step B, the thiophene-diester compound of formula (2a-1) obtained in step A is hydrolyzed in the The base may be sodium hydroxide and potassium hydroxide, and employed in an amount of 2 to 4 molar equivalents based on the amount of the thiophene-diester compound of formula (2a-1).

The reaction may be carried out at a temperature ranging from 0° C. to the boiling point of the solvent used, preferably from room temperature to the boiling point of the solvent.

<Step C>

In step C, the thiophene-dicarboxylic acid derivative of formula (2a-2) obtained in step B is reduced with a reducing agent in a solvent to obtain the thiophene-diol of formula (2b), the compound of formula (2) wherein $R_1$ and $R_2$ are $CH_2X$ and $CH_2Y$, respectively, and X and Y are hydroxy.

The solvent may be preferably tetrahydrofuran, and a preferred example of the reducing agent is borane in the form of a complex with dimethylsulfide or tetrahydrofuran and it may be employed in an amount of 1 to 10 molar equivalents, preferably 4 to 8 molar equivalents, based on the amount of the thiophene-dicarboxylic acid derivative of formula (2a-2).

The reaction may be carried out at a temperature ranging from −20° C. to the boiling point of the solvent used, preferably from room temperature to the boiling point of the solvent.

<Step D>

Alternative to carrying out steps B and C, the thiophene-diester derivative of formula (2a-1) obtained in step A may be directly reduced with a reducing agent in a solvent to obtain the thiophene-diol of formula (2b), as shown in step D.

In this step, diethyl ether, tetrahydrofuran, dioxane, n-hexane, benzene and toluene may be employed as the solvent, and particularly diethyl ether and tetrahydrofuran are preferred.

As the reducing agent, lithium borohydride, a mixture of sodium borohydride with lithium chloride or lithium bromide, lithium aluminum hydride may be employed, and when lithium borohydride or sodium borohydride is used, trimethylborate may be further added thereto. Lithium aluminum hydride may be employed in an amount of 0.5 to 2 molar equivalents, and lithium borohydride or sodium borohydride may be employed in an amount of 1 to 5 molar equivalents, based on the amount of the thiophene-diester derivative of formula (2a-1). The amount of lithium chloride or lithium bromide may be employed in an amount ranging from 1 to 2 molar equivalents per mole of sodium borohydride used. Further, trimethylborate may be used in an amount ranging from 0.05 to 0.2 molar equivalents per mole of sodium borohydride used.

The reaction may be carried out at a temperature ranging from room temperature to the boiling point of the solvent.

<Step E>

In step E, the thiophene-diol derivative of formula (2b) is treated with a halogenating or sulfonylating agent in a solvent to obtain the substituted thiophene derivative of formula (2e), the compound of formula (2) wherein $R_1$ and $R_2$ are $CH_2X$ and $CH_2Y$, respectively, and X and Y are chloro, bromo, methanesulfonyl or p-toluenesulfonyl.

The solvent used in the halogenation may be an aprotic solvent such as tetrahydrofuran, dioxane, 1,2-dimethoxyethane, dichloromethane, chloroform, 1,2-dichloroethane, acetonitrile, propionitrile, and butyronitrile, preferred being dichloromethane, chloroform, and acetonitrile. Representative examples of the halogenating agent include triphenylphosphine dibromide, triphenylphosphine dichloride, thionyl chloride, sulfuryl chloride, phosphorus oxychloride, phosphorus tribromide, phosphorus trichloride, phosphorus pentabromide, and phosphorus pentachloride, preferred being triphenylphosphine dibromide, and triphenylphosphine dichloride. The halogenating agent may be employed in an amount of 2 to 3 molar equivalents based on the amount of the thiophene-diol derivative of formula (2b).

A base may be added in the halogenation reaction, and representative examples thereof include pyridine, picoline, triethylamine, diisopropylethylamine, and tributylamine. The base may be employed in an amount sufficient to neutralize free hydrochloric or hydrobromic acid generated during the reaction.

The halogenation reaction may be carried out at a temperature ranging from −40° C. to the boiling point of the solvent used, preferably from 0° C. to room temperature.

In case a sulfonylation reaction is carried out, the solvent may be an aprotic solvent selected from tetrahydrofuran, dioxane, 1,2-dimethoxyethane, dichloromethane, chloroform, 1,2-dichloroethane and acetonitrile, or a mixture thereof with water. Preferred solvents are dichloromethane, chloroform, and 1,2-dichloroethane. Representative examples of the sulfonylating agent may include methanesulfonyl chloride, benzenesulfonyl chloride, p-toluenesulfonyl chloride, and other substituted benzenesulfonyl chloride. The sulfonylating agent may be employed in an amount of 1 to 2 molar equivalents based on the amount of the thiophene-diol derivative of formula (2b).

A base may be used in the sulfonylation reaction, examples of which include an organic base such as triethylamine, diisopropylethylamine, tributylamine, pyridine, and picoline, and an inorganic base such as sodium hydride, sodium hydroxide, sodium hydrogen carbonate, sodium carbonate, potassium hydrogen carbonate, potassium hydroxide, potassium carbonate, sodium hydrogen phosphate and potassium hydrogen phosphate. The base may be preferably employed in an amount of 1 to 2 molar equivalents based on the amount of sulfonylating agent used.

The sulfonylation reaction may be accelerated in the presence of a catalytic amount of a quaternary ammonium salt such as tetrabutylammonium chloride. The sulfonylation may be carried out at a temperature ranging from 30° C. to the boiling point of the solvent used, preferably from −10° C. to room temperature.

Further, the compound of formula (2) used as an intermediate in the inventive method may be prepared according to Reaction Scheme 3:

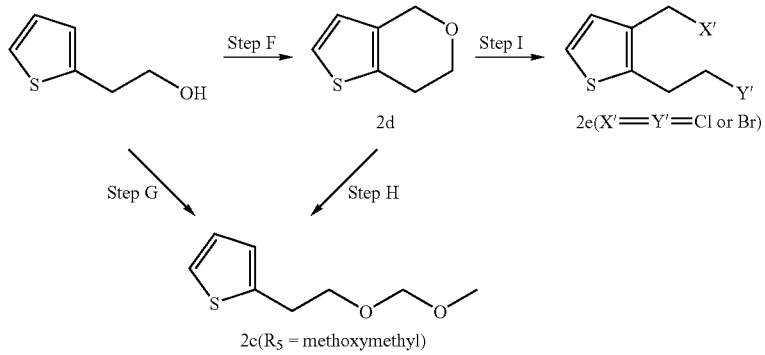

<Step F>

First, 2-thiopheneethanol is allowed to react with a formylating agent in a solvent in the presence of a Lewis acid to obtain the 6,7-dihydrothieno[3,2-c]pyran of formula (2d), the compound of formula (2) wherein $R_1$ and $R_2$ are connected each other to form —$CH_2$—O—$CH_2$—.

In this reaction, the solvent may be an aprotic solvent such as tetrahydrofuran, dioxane, 1,2-dimethoxyethane, 1,2-dichloroethane, acetonitrile, propionitrile, and butyronitrile, preferred being acetonitrile and propionitrile. Representative examples of the Lewis acid are indium(III) chloride, indium (III) bromide, indium(III) triflate, magnesium bromide and tin(IV) chloride, and particularly, indium(III) chloride and magnesium bromide are preferred. The Lewis acid may be employed in an amount of 0.01 to 1 molar equivalent in case an indium salt is used, and in an amount of 1 to 5 molar equivalents in case the other salts are used, based on the amount of 2-thiopheneethanol. Further, p-toluenesulfonic acid may be added to the reactants in a catalytic amount.

The formylating agent may be a formaldehyde solution, paraformaldehyde, 1,3-dioxolane, 1,3,5-trioxane, dimethoxymethane, and diethoxymethane, preferred particularly being paraformaldehyde. It may be employed in an amount of 1 to 3 molar equivalents based on the amount of 2-thiopheneethanol.

The reaction may be carried out at a temperature ranging from room temperature to the boiling point of the solvent used, preferably from 50° C. to the boiling point of the solvent.

Alternative to carrying out Step F, 2-thiopheneethanol may be treated with alkoxymethane derivatives, and then, subjected the product to cyclization to form the compound of formula (2d).

<Step G>

In Step G, 2-thiopheneethanol is allowed to react (i) with a lower alkoxymethane such as dimethoxymethane in the presence of p-toluenesulfonic acid, or (ii) with a lower alkoxymethyl halide such as methoxymethyl chloride, ethoxymethyl chloride, and 2-methoxyethoxymethyl chloride in the presence of a base, to obtain the compound of formula (2c), the compound of formula (2) wherein $R_1$ is hydrogen and $R_2$ is $CH_2OR_5$, $R_5$ being methoxymethyl.

Reaction (i) may be conducted in an organic solvent such as benzene, toluene, tetrahydrofuran, dioxane, 1,2-dimethoxyethane, chloroform, 1,2-dichloroethane and acetonitrile, preferably with an excess amount of a lower dialkoxymethane in the absence of a solvent.

p-Toluenesulfonic acid is used in reaction (i) in a catalytic amount, and lithium bromide or lithium chloride may be added to the reaction mixture in a catalytic amount so as to accelerate reaction (i).

The reaction may be carried out at a temperature ranging from room temperature to the boiling point of the solvent used, preferably from 50° C. to the boiling point of the solvent.

Further, reaction (ii) may be conducted in a solvent such as tetrahydrofuran, dioxane, 1,2-dimethoxyethane, chloroform, 1,2-dichloroethane and acetonitrile. The alkoxymethyl halide may be employed in an amount ranging from 1 to 2 molar equivalents based on the amount of the 2-thiopheneethanol.

The base, which may be employed in reaction (ii), may be an organic base such as triethylamine, diisopropylethylamine, tributylamine, pyridine, and picoline, or an inorganic base such as sodium hydrogen carbonate, sodium carbonate, potassium hydrogen carbonate, and potassium carbonate. The base may be employed in an amount of 1 to 3 molar equivalents based on the amount of 2-thiopheneethanol.

The reaction (ii) may be carried out at a temperature ranging from 0° C. to the boiling point of the solvent used, preferably from room temperature to 70° C.

<Step H>

In Step H wherein the compound of formula (2c) is cyclized, the compound of formula (2c) obtained in Step G is subjected to a ring formation reaction in a solvent in the presence of a Lewis acid to provide the dihydrothieno[3,2-c]pyran of formula (2d).

The solvent used in this step may be an aprotic solvent such as tetrahydrofuran, dioxane, 1,2-dimethoxyethane, dichloromethane, chloroform, 1,2-dichloroethane, acetonitrile, propionitrile and butyronitrile, and preferred solvents are dichloromethane, chloroform, and 1,2-dichloroethane.

Representative examples of the Lewis acid include indium (III) chloride, indium(III) bromide, indium(III) triflate, magnesium bromide, lithium bromide, lithium chloride and tin (IV) chloride, and particularly, indium(III) chloride and magnesium bromide are preferred. An indium salt may be employed in an amount of 0.01 to 1 molar equivalent, and the other may be employed in an amount of 1 to 5 molar equivalents, based on the amount of the compound of formula (2c).

The reaction may be carried out at a temperature ranging from room temperature to the boiling point of the solvent used, preferably from 40° C. to the boiling point of the solvent.

<Step I>

In Step I, dihydrothieno[3,2-c]pyran of formula (2d) is allowed to react with a halogenating agent in the presence or absence of a Lewis acid to obtain a substituted thiophene derivative of formula (2e), the compound of formula (2) wherein $R_1$ and $R_2$ are $CH_2X'$ and $CH_2Y'$, X' and Y' being chloro or bromo.

This reaction may be conducted in a solvent which may be an aprotic solvent such as tetrahydrofuran, dioxane, 1,2-dimethoxyethane, dichloromethane, chloroform, 1,2-dichloroethane, acetonitrile, propionitrile, and butyronitrile, preferred being dichloromethane, chloroform, and acetonitrile.

Representative examples of the halogenating agent include triphenylphosphine dibromide, triphenylphosphine dichloride, phosphorus tribromide, phosphorus trichloride, phosphorus pentabromide and phosphorus pentachloride, preferred being triphenylphosphine dibromide and triphenylphosphine dichloride. The halogenating agent may be employed in an amount of 1 to 2 molar equivalents based on the amount of the thienopyran derivative of formula (2d).

When a Lewis acid is used, it may be zinc chloride or zinc bromide.

The halogenation reaction may be carried out at a temperature ranging from −40° C. to the boiling point of the solvent used, preferably from 0° C. to room temperature.

In accordance with the present invention, the substituted thiophene compound of formula (2e) is allowed to react with a 2-chlorobenzylamine derivative of formula (3) or its salt in a solvent in the presence of a base to obtain a thieno[3,2-c] pyridine derivative of formula (1), as shown in Reaction Scheme 4:

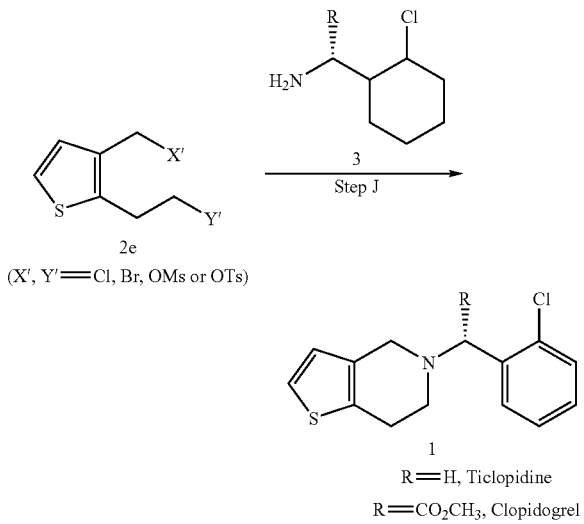

In this reaction, representative examples of the solvent are tertiary alcohols such as t-butanol and amyl alcohol; ethers such as diisopropyl ether, tetrahydrofuran and dioxane; nitriles such as acetonitrile, propionitrile and butyronitrile;

esters such as methyl acetate, ethyl acetate and isopropyl acetate; hydrocarbons; N,N-dimethyl formide and N,N-diethyl acetamide; toluene; and dimethyl sulfoxide; acetonitrile and propionitrile being preferred.

The base which may be employed in the above reaction is an organic base such as triethylamine, diisopropylethylamine, tributylamine, pyridine, and picoline, or an inorganic base such as sodium hydrogen carbonate, sodium carbonate, potassium hydrogen carbonate, potassium carbonate, sodium hydrogen phosphate, and potassium hydrogen phosphate. The base may be preferably employed in an amount of 2 to 5 molar equivalents based on the amount of the substituted thiophene derivative of formula (2e).

The 2-chlorobenzylamine derivative of formula (3) or its salt is preferably employed in an amount of 1 to 2 molar equivalents based on the amount of the substituted thiophene derivative of formula (2e).

The above reaction may be carried out at a temperature ranging from room temperature to the boiling point of the solvent used, preferably from 40° C. to the boiling point of the solvent.

The thieno[3,2-c]pyridine derivatives of the present invention, i.e., ticlopidine and clopidogrel, may be easily converted to ticlopidine hydrochloride and clopidogrel bisulfate, respectively, which are useful active ingredients for antithrombotic drugs.

The following Preparation and Examples are given for the purpose of illustration only and are not intended to limit the scope of the invention.

EXAMPLE 1

Synthesis of methyl 2-methoxycarbonylmethylthiophen-3-carboxylate (Compound of Formula 2a)

100.0 g of dimethyl 1,3-acetonedicarboxylate was dissolved in 2,800 ml of dioxane, and added thereto were 52.5 g of 2,5-dihydroxy-1,4-dithiane and 5.0 g of lithium bromide. The resulting mixture was refluxed for 15 hours, cooled to room temperature, and concentrated by evaporation. To the residue, 1,000 ml of n-hexane was added, stirred, and the hexane layer was separated. This extraction procedure was repeated twice using 500 ml portions of n-hexane. The separated n-hexane layers were combined and concentrated under reduced pressure to obtain 60.9 g (yield of 49%) of the title compound as an oil, which was directly used in the next step without any purification. An analytical sample of the title compound could be obtained by vacuum distillation.

Boiling point: 120~122° C. (0.5 mmHg)
$^1$H-NMR (CDCl$_3$, ppm): δ 3.73 (s, 3H), 3.83 (s, 3H), 4.22 (s, 2H), 7.15 (d, 1H, J=5.6 Hz), 7.44 (d, 1H, J=5.6 Hz)
$^{13}$C-NMR (CDCl$_3$, ppm): δ 34.7, 52.0, 52.7, 123.7, 129.4, 129.9, 144.3, 164.0, 170.8
MS (EI, m/z): 214(M+), 182

EXAMPLE 2

Synthesis of 2-(3-hydroxymethylthiophen-2-yl)ethanol (Compound of Formula 2b)

In a dried vessel, 600 mg of lithium aluminum hydride was charged under a nitrogen atmosphere, and then 26 mL of anhydrous tetrahydrofuran was added thereto. To the resulting suspension, a solution of 2.8 g of the compound obtained in Example 1 dissolved in 10 mL of tetrahydrofuran was added over about 5 minutes. The resulting mixture was stirred at room temperature for 1 hour, and then refluxed for 1 hour. The reaction solution was cooled to 0° C., and 0.5 mL of water, 0.5 mL of 15% sodium hydroxide aqueous solution, and 4 mL of water were added thereto slowly in succession. The resulting mixture was stirred for about 1 hour, and the insoluble materials was filtered and washed with 30 mL of tetrahydrofuran. Combined filtrate was concentrated by evaporation under reduced pressure to obtain 1.8 g (yield of 87%) of oily title compound.

$^1$H-NMR (CDCl$_3$, ppm): δ 2.98 (t, 2H, J=5.7 Hz), 3.69 (t, 2H, J=5.7 Hz), 3.93 (brs, 1H), 4.10 (brs, 1H), 4.43 (s, 2H), 6.93 (d, 1H, J=5.1 Hz), 7.08 (d, 1H, J=5.1 Hz).
$^{13}$C-NMR (CDCl$_3$, ppm): δ 31.2, 57.7, 63.3, 123.2, 129.4, 138.9, 139.1
MS (EI, m/z): 158(M+), 110.

EXAMPLE 3

Synthesis of 2-(3-hydroxymethylthiophen-2-yl)ethanol (Compound of Formula 2b)

To 800 mL of anhydrous tetrahydrofuran, 31.0 g of sodium boron hydride and 71.3 g of lithium bromide were added, and then 10.6 mL of trimethyl borate was added thereto dropwise at 0° C. The resulting mixture was stirred at room temperature for 30 minutes, and then a solution obtained by dissolving 70.4 g of the compound obtained in Example 1 in 200 mL of tetrahydrofuran was slowly added over 2 hours while allowing the resulting mixture to reflux. The reaction solution was further refluxed for 2 hours then cooled to room temperature. 100 mL of anhydrous methanol was added slowly to the solution, and then 700 mL of ethyl ether and 700 mL of water were added. The organic phase was collected, dried over anhydrous magnesium sulfate, and concentrated under reduced pressure to obtain 47.1 g (yield of 90%) of the title compound as an oil.

The analysis data of the compound thus obtained were the same as in Example 2.

EXAMPLE 4

Synthesis of 2-carboxymethylthiophen-3-carboxylic acid (Compound of Formula 2a)

13.0 g of the compound obtained in Example 1 was dissolved in 260 mL of methanol, and a solution obtained by dissolving 4.84 g of sodium hydroxide in 26 mL of water was added thereto. The resulting solution was refluxed for 4 hours, cooled to room temperature, concentrated under reduced pressure to remove methanol. The resulting aqueous solution was washed with 10 ml of diethyl ether and acidified to pH 2 to 3 using concentrated HCl. The solids thus solidified were filtered, washed with a small amount of cold water and dried at 40° C. to obtain 9.60 g (yield of 85%) of the title compound as a brown solid.

Melting point: 212~213° C.
$^1$H-NMR (CD$_3$COCD$_3$, ppm): δ 4.26 (s, 2H), 7.39 (d, 1H, J=5.4 Hz), 7.42 (d, 1H, J=5.4 Hz).

EXAMPLE 5

Synthesis of 2-(3-hydroxymethylthiophen-3-yl)ethanol (Compound of Formula 2b)

0.45 g of the compound obtained in Example 4 was dissolved in 10 mL of anhydrous tetrahydrofuran, and the resulting solution was cooled to −2° C. 3.7 mL of 2M solution of borane-dimethylsulfide complex in tetrahydrofuran was slowly added thereto, and the resulting mixture was allowed to react for at least 1 hour at −1° C. The reaction mixture was warmed to room temperature and further added thereto was 3.7 mL of a 2M solution of borane-dimethylsulfide complex in tetrahydrofuran. The resulting mixture was kept at room temperature for 2 hours, and cooled to 0° C. After adding water thereto, the resulting solution was extracted three times with 15 mL portions of ethyl acetate, and the organic layers were combined, washed with 20 ml of water, dried over anhydrous magnesium sulfate and concentrated under reduced pressure to obtain 0.22 g (yield of 57%) of the title compound as an oil.

The analysis data of the compound thus obtained were the same as in Example 2.

EXAMPLE 6

Synthesis of
2-(3-hydroxymethylthiophen-2-yl)ethanol
(Compound of Formula 2b)

0.50 g of the compound obtained in Example 4 was dissolved in 10 mL of anhydrous tetrahydrofuran, and the resulting solution was cooled to −20° C. 4 mL of 1.5M solution of borane-tetrahydrofuran complex in tetrahydrofuran was slowly added thereto, and the resulting mixture was allowed to react for at least 1 hour at −10° C. The reaction solution was warmed to room temperature and 4.5 mL of 1.5M solution of borane-tetrahydrofuran complex in tetrahydrofuran was further added thereto. The resulting mixture was kept at room temperature for 1 hour. Thereafter, the procedure of Example 5 was repeated to obtain 0.37 g (yield of 87%) of the title compound as an oil.

The analysis data of the compound thus obtained were the same as in Example 2.

EXAMPLE 7

Synthesis of
2-(2-bromoethyl)-3-bromomethylthiophene
(Compound of Formula 2e)

2.0 g of the compound obtained in Example 2 was dissolved in 40 mL of dichloromethane, and the resulting solution was cooled to below 5° C. 13.4 g of triphenylphosphine dibromide was added thereto, and the resulting mixture was warmed to room temperature, stirred for 4 hours, and concentrated by evaporation under reduced pressure. To the residue, 5 mL of ethyl acetate and then 15 mL of n-hexane were added. The resulting mixture was stirred for 1 hour at room temperature and 2 hours at below 5° C., filtered and condensed under reduced pressure. The residue was subjected to silica gel column chromatography (eluent, n-hexane:ethyl acetate=10:1) to obtain 2.9 g (yield of 80%) of the title compound as a yellowish oil.

$^1$H-NMR (CDCl$_3$, ppm): δ 3.38 (t, 2H, J=7.2 Hz), 3.59 (t, 2H, J=7.2 Hz), 4.49 (s, 2H), 7.02 (d, 1H, J=5.1 Hz), 7.18 (d, 1H, J=5.1 Hz)

$^{13}$C NMR (CDCl$_3$, ppm): δ 25.8, 31.7, 32.0, 124.3, 129.5, 135.2, 139.7

MS (EI, m/z): 286, 284, 282, 205, 203

EXAMPLE 8

Synthesis of
2-(2-bromoethyl)-3-bromomethylthiophene
(Compound of Formula 2e)

17.8 g of triphenylphosphine was dissolved in 40 mL of dichloromethane, and the resulting solution was cooled to below 5° C. 10.6 g of bromine was added thereto slowly over 10 minutes. The resulting mixture was stirred for 30 minutes at room temperature, and a solution of 5.0 g of the compound obtained in Example 2 in 20 mL of dichloromethane was added thereto slowly. The resulting mixture was stirred at room temperature for 4 hours and concentrated by evaporation under reduced pressure. To the residue, 40 mL of ethyl acetate and then 120 mL of n-hexane were added, and the resulting mixture was stirred for 1 hour at room temperature and 2 hours at below 5° C. Insoluble materials were filtered off and the filtrate was concentrated under reduced pressure to obtain 7.8 g (yield of 87%) of the title compound as a yellowish oil.

The analysis data of the compound thus obtained were the same as in Example 7.

EXAMPLE 9

Synthesis of
2-(2-bromoethyl)-3-bromomethylthiophene
(Compound of Formula 2e)

10.7 g of triphenylphosphine was dissolved in 40 mL of acetonitrile, and the resulting solution was cooled to below 5° C. and 6.4 g of bromine was added thereto slowly over 10 minutes. The resulting mixture was warmed to room temperature and stirred for 1 hour, and then solution of 3.0 g of the compound obtained in Example 2 in 15 mL of acetonitrile was added. The resulting mixture was stirred at room temperature for 4 hours and concentrated by evaporation under reduced pressure. To the residue, 20 mL of ethyl acetate and then 40 mL of diisopropyl ether were added, and the resulting mixture was stirred for 1 hour at room temperature and 2 hours at below 5° C. Insoluble materials were filtered off and the filtrate was concentrated under reduced pressure. The residue was subjected to silica gel column chromatography (eluent, n-hexane:ethyl acetate=10:1) to obtain 3.5 g (yield of 65%) of the title compound as a yellowish oil.

The analysis data of the compound thus obtained were the same as in Example 7.

EXAMPLE 10

Synthesis of
2-(2-bromoethyl)-3-bromomethylthiophene
(Compound of Formula 2e)

5.0 g of the compound obtained in Example 2 was dissolved in 95 mL of chloroform, and 17.1 g of phosphorus tribromide was added thereto at below 5° C. The resulting mixture was warmed to room temperature, stirred for 15 hours and washed twice with 100 mL portions of water. The organic layer was dried over anhydrous magnesium sulfate and condensed under reduced pressure. The residue was subjected to a silica gel column chromatography (eluent, n-hexane:ethyl acetate=10:1) to obtain 4.3 g (yield of 48%) of the title compound as a yellowish oil.

The analysis data of the compound thus obtained were the same as in Example 7.

EXAMPLE 11

Synthesis of
2-(2-chloroethyl)-3-chloromethylthiophene
(Compound of Formula 2e)

3.0 g of the compound obtained in Example 2 was dissolved in 57 mL of dichloromethane, and the resulting solution was cooled to −3° C. To the solution, 6.1 g of diisopropylethylamine and 3.1 g of sulfuryl chloride were added, and the resulting mixture was stirred for 30 min at the same temperature and for an hour at room temperature. 20 mL of dichloromethane was added to the reaction solution, and the resulting mixture was washed twice with 40 mL portions of water. The organic layer was dried over anhydrous magnesium sulfate and concentrated under reduced pressure. The residue was subjected to a silica gel column chromatography (eluent, n-hexane:ethyl acetate=10:1) to obtain 1.0 g (yield of 27%) of the title compound as a colorless oil.

$^1$H-NMR (CDCl$_3$, ppm): δ 3.30 (t, 2H, J=7.3 Hz), 7.27 (t, 2H, J=7.3 Hz), 4.59 (s, 2H), 7.02 (d, 1H, J=5.2 Hz), 7.18 (d, 1H, J=5.2 Hz).

$^{13}$C-NMR (CDCl$_3$, ppm): δ 32.0, 39.4, 45.3, 124.8, 129.7, 135.7, 139.2.

MS (EI, m/z): 194(M+), 159, 145

EXAMPLE 12

Synthesis of 3-chloromethyl-2-(2-methanesulfonyloxyethyl)thiophene (Compound of Formula 2e)

2.0 g of the compound obtained in Example 2 was dissolved in 35 mL of dichloromethane, and the resulting solution was cooled to below 5° C. To the solution, 3.0 g of methanesulfonyl chloride and 4.1 g of diisopropylethylamine were added, and the resulting mixture was stirred for 30 minutes. 30 mL of dichloromethane was added to the reaction solution, and the resulting mixture was washed twice with 30 mL portions of water. The organic layer was dried over anhydrous magnesium sulfate and concentrated under reduced pressure to obtain 2.9 g (yield of 91%) of the title compound as an oil.

$^1$H-NMR (CDCl$_3$, ppm): δ 3.03 (s, 3H), 3.38 (t, 2H, J=6.6 Hz), 4.50 (t, 2H, J=6.6 Hz), 4.66 (s, 2H), 7.11 (d, 1H, J=5.2 Hz), 7.27 (d, 1H, J=5.2 Hz).

$^{13}$C-NMR (CDCl$_3$, ppm): δ 28.1, 37.7, 38.9, 69.8, 124.6, 129.4, 135.6, 136.8

EXAMPLE 13

Synthesis of 3-chloromethyl-2-(2-p-toluenesulfonyloxyethyl)thiophene (Compound of Formula 2e)

1.5 g of the compound obtained in Example 2 was dissolved in 40 mL of dichloromethane, and the resulting solution was cooled to below 5° C. To the solution, 3.6 g of p-toluenesulfonyl chloride and 1.9 g of triethylamine were added dropwise, and the resulting mixture was warmed to room temperature, stirred for 6 hours and washed twice with 20 ml portions of water. The organic layer was dried over anhydrous magnesium sulfate and concentrated under reduced pressure. The residue was subjected to a silica gel column chromatography (eluent, n-hexane:ethyl acetate=10:1) to obtain 1.5 g (yield of 48%) of the title compound as an oil.

$^1$H-NMR (CDCl$_3$, ppm): δ 2.41 (s, 3H), 3.16 (t, 2H, J=6.8 Hz), 4.18 (t, 2H, J=6.8 Hz), 4.46 (s, 2H), 6.94 (d, 1H, J=5.2 Hz), 7.10 (d, 1H, J=5.2 Hz), 7.29 (d, 2H, J=8.2 Hz), 7.71 (d, 2H, J=8.2 Hz)

$^{13}$C-NMR (CDCl$_3$, ppm): δ 22.0, 27.9, 38.8, 70.1, 124.4, 128.2, 129.2, 130.3, 133.0, 135.5, 136.7, 145.9

EXAMPLE 14

Synthesis of 6,7-dihydro-4H-thieno[3,2-c]pyrane (Compound of Formula 2d)

20.0 g of 2-thiopheneethanol, 6.1 g of paraformaldehyde, and 1.7 g of indium(III) chloride were added to 1,500 mL of acetonitrile, and the resulting mixture was refluxed for 2 hours. The reaction solution was cooled to room temperature and concentrated by evaporation under reduced pressure. The residue thus obtained was distilled under reduced pressure to obtain 14.4 g (yield of 66%) of the title compound as an oil form.

Boiling point: 88~90° C. (8 mmHg)

$^1$H-NMR (CDCl$_3$, ppm): δ 2.88 (t, 2H, J=5.5 Hz), 3.97 (t, 2H, J=5.5 Hz), 4.73 (s, 2H), 6.73 (d, 1H, J=5.1 Hz), 7.11 (d, 1H, J=5.1 Hz)

$^{13}$C NMR (CDCl$_3$, ppm): δ 26.3, 65.7, 67.3, 123.5, 124.4, 133.0, 134.5

MS (EI, m/z) 140(M+), 110

EXAMPLE 15

Synthesis of 6,7-dihydro-4H-thieno[3,2-c]pyrane (Compound of Formula 2d)

10.0 g of 2-thiopheneethanol, 2.8 g of paraformaldehyde, and 2.2 g of indium(III) triplate were added to 780 mL of acetonitrile, and the resulting mixture was refluxed for 12 hours. The reaction product solution was cooled to room temperature and concentrated by evaporation under reduced pressure. The residue was distilled under reduced pressure to obtain 4.7 g (yield of 43%) of the title compound, of which analysis data were the same as obtained in Example 14.

EXAMPLE 16

Synthesis of 6,7-dihydro-4H-thieno[3,2-c]pyrane (Compound of Formula 2d)

10.0 g of 2-thiopheneethanol, 5.9 g of paraformaldehyde, and 28.7 g of magnesium bromide were added to 780 mL of acetonitrile, and the resulting mixture was refluxed for 24 hours. The reaction product solution was cooled to room temperature and concentrated by evaporation under reduced pressure. To the residue, 100 mL of water and 150 mL of n-hexane were added, and the resulting mixture was stirred for 5 minutes. The organic layer was separated and dried over anhydrous magnesium sulfate, and then concentrated under reduced pressure. The residue was distilled under reduced pressure to obtain 4.7 g (yield of 43%) of the title compound, of which analysis data were the same as obtained in Example 14.

EXAMPLE 17

Synthesis of 6,7-dihydro-4H-thieno[3,2-c]pyrane (Compound of Formula 2d)

10.0 g of 2-thiopheneethanol, 3.5 g of 1,3,5-trioxane, and 862 mg of indium(III) chloride were added to 1,500 mL of butyronitrile, and the resulting mixture was refluxed for 6 hours. The reaction product solution was cooled to room temperature and concentrated by evaporation under reduced pressure. The residue was distilled under reduced pressure to obtain 6.6 g (yield of 60%) of the title compound, of which analysis data were the same as obtained in Example 14.

EXAMPLE 18

Synthesis of 6,7-dihydro-4H-thieno[3,2-c]pyrane (Compound of Formula 2d)

10.0 g of 2-thiopheneethanol, 11.5 g of 1,3-dioxolane, and 862 mg of indium(III) chloride were added to 780 mL of acetonitrile, and the resulting mixture was refluxed for 10 hours. The reaction product solution was cooled to room temperature and concentrated by evaporation under reduced pressure. To the residue, 100 mL of water and 150 mL of n-hexane were added, and the resulting mixture was stirred for 5 minutes. The organic layer was separated and dried over anhydrous magnesium sulfate, and then concentrated under reduced pressure. The residue was distilled under reduced pressure to obtain 6.6 g (yield of 60%) of the title compound, of which analysis data were the same as obtained in Example 14.

EXAMPLE 19

Synthesis of 2-(2-methoxymethoxyethyl)thiophene (Compound of Formula 2c)

150 g of 2-thiopheneethanol was dissolved in 2,250 mL of dimethoxymethane, and 22.3 g of p-toluenesulfonic acid and 20.3 g of lithium chloride were added thereto. The resulting mixture was refluxed for 5 hours and concentrated by evaporation under reduced pressure. To the residue, 1,000 mL of water and 1,500 mL of n-hexane were added, and the resulting mixture was stirred for 5 minutes. Aqueous layer was discarded, and the organic layer was washed twice with 700 mL portions of water, dried over anhydrous magnesium sulfate and concentrated under reduced pressure to obtain 193 g (yield of 96%) of the title compound as a colorless oil.

$^1$H-NMR (CDCl$_3$, ppm): δ 3.15 (t, 2H, J=6.6 Hz), 3.37 (s, 3H), 3.80 (t, 2H, J=6.6 Hz), 4.67 (s, 2H), 6.87-6.93 (m, 1H), 6.96 (dd, 1H, J=5.1, 3.4 Hz), 7.17 (dd, 1H, J=5.1, 1.0 Hz)

EXAMPLE 20

Synthesis of 2-[2-(2-methoxyethoxymethoxy)ethyl]thiophene (Compound of Formula 2c)

15.0 g of 2-thiopheneethanol was dissolved in 350 mL of dichloromethane, and 30.2 g of diisopropylamine was added thereto. The resulting mixture was cooled to 0° C. and 17.5 g of 2-methoxyethoxymethyl chloride was added thereto. The resulting mixture was stirred for 2 hours and heated to reflux for 2 hours. The reaction product solution was cooled and concentrated by evaporation under reduced pressure. To the residue, 200 mL of water and 250 mL of n-hexane were added, and the resulting mixture was stirred for 5 minutes. Aqueous layer was discarded, and the organic layer was washed twice with 700 mL portions of water, dried over anhydrous magnesium sulfate and concentrated under reduced pressure to obtain 21.5 g (yield of 85%) of the title compound as a colorless oil.

$^1$H-NMR (CDCl$_3$, ppm): δ 3.07 (t, 2H, J=6.6 Hz), 3.34 (s, 3H), 3.44-3.52 (m, 2H), 3.58-3.64 (m, 2H), 3.76 (t, 2H, J=6.6 Hz), 4.70 (s, 2H), 6.80-6.83 (m, 1H), 6.88 (dd, 1H, J=5.1, 3.4 Hz), 7.09 (dd, 1H, J=5.1, 1.1 Hz)

EXAMPLE 21

Synthesis of 6,7-dihydro-4H-thieno[3,2-c]pyrane (Compound of Formula 2d)

61.2 g of 2-(2-methoxymethoxyethyl)thiophene obtained in Example 19 and 130.8 g of magnesium bromide were added to 850 mL of dichloromethane, and the resulting mixture was refluxed for 2 hours. The reaction product solution was cooled to room temperature and concentrated by evaporation under reduced pressure. To the residue, 500 mL of water and 800 mL of n-hexane were added, and the resulting mixture was stirred for 5 minutes. Aqueous layer was discarded, and the organic layer was washed twice with 300 mL portions of water, dried over anhydrous magnesium sulfate and concentrated under reduced pressure. The residue was distilled under reduced pressure to obtain 40.7 g (yield of 82%) of the title compound, of which analysis data were the same as obtained in Example 14.

EXAMPLE 22

Synthesis of 6,7-dihydro-4H-thieno[3,2-c]pyrane (Compound of Formula 2d)

11.0 g of 2-[2-(2-methoxyethoxymethoxy)ethyl] thiophene obtained in Example 20 and 1.1 g of indium(III) chloride were added to 750 mL of acetonitrile, and the resulting mixture was refluxed for 5 hours. The reaction product solution was cooled to room temperature and concentrated by evaporation under reduced pressure. To the residue, 100 mL of water and 150 mL of n-hexane were added, and the resulting mixture was stirred for 5 minutes. Aqueous layer was discarded, and the organic layer was washed twice with 70 mL portions of water, dried over anhydrous magnesium sulfate and concentrated under reduced pressure. The residue was distilled under reduced pressure to obtain 2.9 g (yield of 41%) of the title compound, of which analysis data were the same as obtained in Example 14.

EXAMPLE 23

Synthesis of 2-(2-bromoethyl)-3-bromomethylthiophene (Compound of Formula 2e)

To a solution of 9.5 g of triphenylphosphine dibromide dissolved in 50 mL of acetonitrile, 2 g of 6,7-dihydro-4H-thieno[3,2-c]pyrane obtained in Example 14 was added, and the resulting mixture was refluxed for 8 hours. The reaction product solution was concentrated by evaporation under reduced pressure. To the residue, 5 mL of ethyl acetate and then 15 mL of n-hexane were added. The resulting mixture was stirred for 1 hour at room temperature and 2 hours at below 5° C., filtered, and concentrated under reduced pressure. The residue was subjected to a silica gel column chromatography (eluent, n-hexane:ethyl acetate=10:1) to obtain 3.3 g (yield of 80%) of the title compound as a yellowish oil, of which analysis data were the same as obtained in Example 7.

EXAMPLE 24

Synthesis of 5-[(2-chlorophenyl)methyl]-4,5,6,7-tetrahydrothieno[3,2-c]pyridine (Compound of Formula 1a; Ticlopidine)

At below 5° C., 5.0 g of 2-(2-bromoethyl)-3-bromomethylthiophene obtained in Example 7 was dissolved in 50 mL of acetonitrile, and added thereto was a solution obtained by dissolving 2.7 g of 2-chlorobenzylamine and 6.8 g of diisopropylethylamine in 25 mL of acetonitrile. The resulting mixture was refluxed for 5 hours, and concentrated by evaporation under reduced pressure. The residue was dissolved in 100 mL of ethyl acetate, and washed twice with 70 mL portions of water. The organic layer was washed with 50 mL of saturated sodium chloride aqueous solution and concentrated under reduced pressure. The dark yellow colored oily residue thus obtained was subjected to a silica gel column chromatography (eluent, n-hexane:ethyl acetate=5:1) to obtain 3.6 g (yield of 78%) of the title compound as a yellowish oil.

$^1$H-NMR (CDCl$_3$, ppm): δ 2.87-2.91 (m, 4H), 3.66 (s, 2H), 3.85 (s, 2H), 6.73 (d, 1H, J=5.0 Hz), 7.09 (d, 1H, J=0.5 Hz), 7.19-7.29 (m, 2H), 7.35-7.42 (m, 1H), 7.52-7.61 (m, 1H).

EXAMPLE 25

Synthesis of methyl (S)-(+)-α-(o-chlorophenyl)-6,7-dihydrothieno[3,2-c]pyridin-5(4H)-acetate (Compound of Formula 1b; Clopidogrel)

5.0 g of 2-(2-bromoethyl)-3-bromomethylthiophene obtained in Example 7 was dissolved in 50 mL of acetonitrile, and added thereto was a solution obtained by dissolving 4.6 g of (S)-(+)-2-(2-chlorophenyl)glycine methyl ester hydrochloride and 6.8 g of diisopropylethylamine in 20 mL of acetonitrile over 30 minutes. The resulting mixture was refluxed for 8 hours, and concentrated by evaporation under reduced pressure. The residue was dissolved in 100 mL of ethyl acetate, and washed twice with 70 mL portions of water. The organic layer was washed with 50 mL of saturated sodium chloride aqueous solution and condensed under reduced pressure. The dark yellow colored oily residue thus obtained was subjected to a silica gel column chromatography (eluent, n-hexane:ethyl acetate=5:1) to obtain 5.0 g (yield of 88%) of the title compound as a yellowish oil.

$^1$H-NMR (CDCl$_3$, ppm): δ 2.89 (s, 4H), 3.60-3.78 (m, 2H), 3.73 (s, 3H), 4.93 (s, 1H), 6.67 (d, 1H, J=5.1 Hz), 7.06 (d, 1H, J=5.1 Hz), 7.26-7.30 (m, 2H), 7.37-7.45 (m, 1H), 7.68-7.77 (m, 1H)

EXAMPLE 26

Synthesis of methyl (S)-(+)-α-(o-chlorophenyl)-6,7-dihydrothieno[3,2-c]pyridin-5(4H)-acetate (Compound of Formula 1b; Clopidogrel)

The procedure of Example 25 was repeated except that t-butanol was employed instead of acetonitrile as a solvent, to obtain the title compound at a yield of 85%.

EXAMPLES 27 AND 28

Synthesis of methyl (S)-(+)-α-(o-chlorophenyl)-6,7-dihydrothieno[3,2-c]pyridin-5(4H)-acetate (Compound of Formula 1b; Clopidogrel)

The procedure of Example 25 was repeated except that triethylamine and potassium carbonate were employed, respectively, instead of diisopropylethylamine as a base, to obtain the title compound at yields of 41% and 78%, respectively.

EXAMPLES 29 TO 31

Synthesis of methyl (S)-(+)-α-(o-chlorophenyl)-6,7-dihydrothieno[3,2-c]pyridin-5(4H)-acetate (Compound of Formula 1b; Clopidogrel)

The procedure of Example 25 was repeated except that 2-(2-chloroethyl)-3-chloromethylthiophene obtained in Example 12, 2-(2-methanesulfonyloxyethyl)thiophene obtained in Example 13 and 2-(2-p-toluenesulfonyloxyethyl) thiophene obtained in Example 14 were employed, respectively, instead of 2-(2-bromoethyl)-3-bromomethylthiophene obtained in Example 7 as a starting material, to obtain the title compound at yields of 85%, 79% and 58%, respectively.

EXAMPLE 32

Synthesis of methyl (S)-(+)-α-(o-chlorophenyl)-6,7-dihydrothieno[3,2-c]pyridin-5(4H)-acetate (Compound of Formula 1b; Clopidogrel)

To a solution of 47.5 g of triphenylphosphine dibromide in 250 ml of acetonitrile, 10 g of 6,7-dihydro-4H-thieno[3,2-c] pyrane was added. The resulting mixture was refluxed for 24 hours, and then added thereto dropwise was a solution obtained by dissolving 14 g of (S)-(+)-2-(2-chlorophenyl) glycine methyl ester hydrochloride and 36 mL of diisopropylethylamine in 100 mL of acetonitrile over 30 minutes while allowing the resulting mixture to reflux. After 8 hours, the reaction product solution was concentrated by evaporation under reduced pressure. To the residue thus obtained, 50 mL of ethyl acetate and 150 mL of n-hexane were added, and the solids thus precipitated were filtered. The filtrate was washed twice with 150 mL portions of water and then with 50 mL of saturated sodium chloride solution. The organic layer was passed through an activated carbon layer and condensed under reduced pressure to obtain 18.6 g (yield of 81%) of the title compound as a yellow oil.

While the embodiments of the subject invention have been described and illustrated, it is obvious that various changes and modifications can be made therein without departing from the spirit of the present invention which should be limited only by the scope of the appended claims.

What is claimed is:

1. A method for preparing a thieno[3,2-c]pyridine derivative of formula (1) comprising reacting a compound of formula (2e) with a compound of formula (3) or its salt:

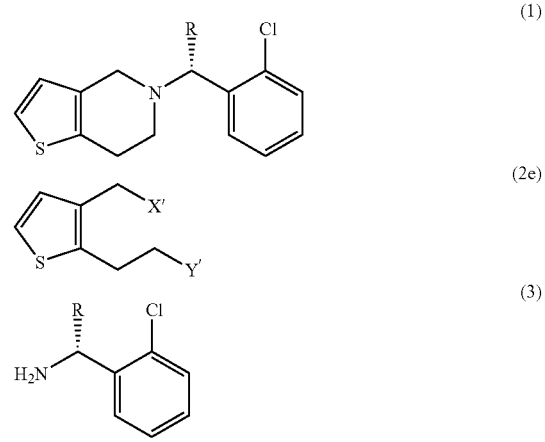

wherein,

R is hydrogen or methoxycarbonyl; and

X' and Y' are each independently chloro, bromo, methanesulfonyloxy or p-toluenesulfonyloxy.

2. The method of claim 1, wherein the compound of formula (2e) is obtained by (a) cyclizing a compound of formula (4) with 2,5-dihydroxy-1,4-dithiane to obtain a compound of formula (2a), (b) reducing the compound of formula (2a) with a reducing agent to obtain a compound of formula (2b), and (c) reacting the compound of formula (2b) with a halogenating or sulfonylating agent:

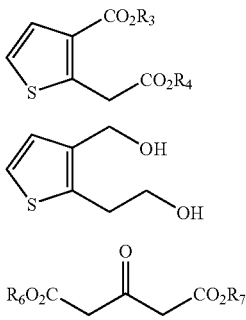

wherein,

R₃ and R₄ are each independently hydrogen or straight or branched $C_{1-6}$ alkyl, and R₆ and R₇ are each independently straight or branched $C_{1-6}$ alkyl.

3. The method of claim 1, wherein a compound of formula (2e) is obtained by (a) cyclizing directly 2-thiopheneethanol with formylating agent, or reacting 2-thiopheneethanol with dialkoxymethane to obtain a compound of formula (2c) and then cyclizing the compound of formula (2c), to obtain the compound of formula (2d) and (b) reacting the compound of formula (2d) with a halogenating agent:

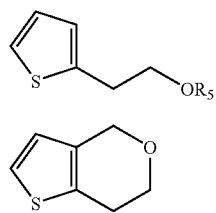

wherein,

R₅ is $C_{1-4}$ alkoxymethyl.

4. The method of claim 1, wherein the compound of formula (3) is 2-chlorobenzylamine or (S)-(+)-2-(2-chlorophenyl)glycine methyl ester, or a salt thereof.

5. The method of claim 1, wherein the compound of formula (3) or its salt is employed in an amount of 1 to 2 molar equivalents based on the amount of the compound of formula (2e).

6. The method of claim 1, wherein the reaction is conducted in an organic solvent in the presence of a base.

7. The method of claim 6, wherein the organic solvent is selected from the group consisting of tertiary alcohols, ethers, nitriles, esters, optionally halogenated hydrocarbons, amides, toluene, dimethylsulfoxide and a mixture thereof.

8. The method of claim 6, wherein the base is an organic base selected from the group consisting of triethylamine, diisopropylethylamine, tributylamine, pyridine, picoline and a mixture thereof, or an inorganic base selected from the group consisting of sodium hydrogen carbonate, sodium carbonate, potassium hydrogen carbonate, potassium carbonate, sodium hydrogen phosphate, potassium hydrogen phosphate and a mixture thereof, or a combination thereof.

9. The method of claim 6, wherein the base is employed in an amount of 2 to 5 molar equivalents based on the amount of the compound of formula (2e).

10. The method of claim 6, wherein the reaction is carried out at a temperature ranging from room temperature to the boiling point of the solvent used.

11. A compound of formula (2e) as an intermediate for the preparation of a thieno[3,2-c]pyridine derivative of formula (1) according to claim 1:

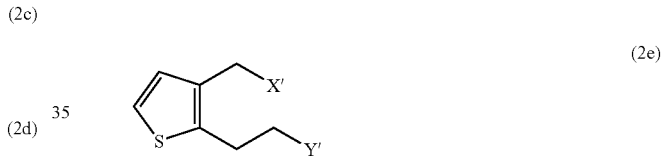

wherein,

X' and Y' are each independently chloro, bromo, methanesulfonyloxy or p-toluenesulfonyloxy.

* * * * *